US009928338B2

(12) United States Patent
Tang et al.

(10) Patent No.: US 9,928,338 B2
(45) Date of Patent: *Mar. 27, 2018

(54) METHOD AND SYSTEM FOR PHASING INDIVIDUAL GENOMES IN THE CONTEXT OF CLINICAL INTERPRETATION

(75) Inventors: Hua Tang, Stanford, CA (US); Michael Snyder, Stanford, CA (US); Jennifer Li-Pook Than, Menlo Park, CA (US); Konrad J. Karczewski, Stanford, CA (US); Nicholas Johnson, Palo Alto, CA (US); Wing H. Wong, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 798 days.

This patent is subject to a terminal disclaimer.

(21) Appl. No.: 13/487,064

(22) Filed: Jun. 1, 2012

(65) Prior Publication Data

US 2013/0085728 A1    Apr. 4, 2013

Related U.S. Application Data

(60) Provisional application No. 61/492,365, filed on Jun. 1, 2011.

(51) Int. Cl.
| | |
|---|---|
| G01N 33/53 | (2006.01) |
| G06F 19/22 | (2011.01) |
| G06F 19/00 | (2018.01) |
| G06F 19/18 | (2011.01) |
| G06F 19/24 | (2011.01) |

(52) U.S. Cl.
CPC .............. *G06F 19/22* (2013.01); *G06F 19/18* (2013.01); *G06F 19/24* (2013.01); *G06F 19/34* (2013.01)

(58) Field of Classification Search
CPC .......... G06F 19/18; G06F 19/24; G06F 19/22; G06F 19/12; G06F 19/28; G06F 19/20; G06F 19/26; G06F 19/16; G06F 19/34; G06F 19/14; G06F 19/363; G06F 3/0481; G06N 5/02; G06Q 50/22
See application file for complete search history.

(56) References Cited

U.S. PATENT DOCUMENTS

| | | | |
|---|---|---|---|
| 2013/0080068 A1* | 3/2013 | Dewey | G06F 19/24 702/19 |
| 2015/0370959 A9 | 12/2015 | Dewey et al. | |

OTHER PUBLICATIONS

US 9,443,056, 09/2016, Dewey et al. (withdrawn)
Browning, B. et al. The American Journal of Human Genetics 84, 210-223, Feb. 13, 2009.*
Paul et al., Genetic Society of America 187:1115-1128 (Apr. 2013).*
Browning et al. Nature Reviews: Genetics vol. 12 (Oct. 2011) pp. 703-714.*
Aji et al, "The Generalized Distributive Law", IEEE Transactions on Information Theory, Mar. 2000, vol. 46, No. 2, pp. 325-343.
Alexander et al., "Fast model-based estimation of ancestry in unrelated individuals", Genome Research, Sep. 2009, vol. 19, pp. 1655-1664.
Bauchet et al., "Measuring European Population Stratification with Microarray Genotype Data", The American Journal of Human Genetics, May 2007, vol. 80, pp. 948-956.
Bellman et al., "On the Approximation of Curves by Line Segments Using Dynamic Programming", Communications of the ACM, 1961, 4(6), 13 pgs.
Bercovici et al., "Inferring Ancestries Efficiently in Admixed Populations with Linkage Disequilibrium", Journal of Computational Biology, 2009, vol. 16, No. 8, pp. 1141-1150.
Best et al., "Active Set Algorithms for Isotonic Regression; A Unifying Framework", Mathematical Programming, 1990, vol. 47, pp. 425-439.
Bigham et al., "Identifying positive selection candidate loci for high-altitude adaptation in Andean populations", Human Genomics, Dec. 2009. 4(2), pp. 79-90.
Blei et al., "Latent Dirichlet Allocation", Journal of Machine Learning Research, 2003, vol. 3, pp. 993-1022.
Boyle et al., "Annotation of functional variation in personal genomes using RegulomeDB", Genome research 22:1790-1797, 2012.
Breiman, "Random Forest", Machine Learning, 2001, vol. 45, pp. 5-32.
Browning et al, "Rapid and Accurate Haplotype Phasing and Missing-Data Inference for Whole-Genome Association Studies by Use of Localized Haplotype Clustering", The American Journal of Human Genetics, Nov. 2007, vol. 81, pp. 1084-1097.
Browning et al., "Efficient Multilocus Association Testing for Whole Genome Association Studies Using Localized Haplotype Clustering", Genetic Epidemiology, 2007, vol. 31, pp. 365-375.
Bryc et al., "Genome-wide patterns of population structure and admixture in West Africans and African Americans", PNAS, Jan. 12, 2010, vol. 107, No. 2, pp. 786-791.
Buntine et al, et al., "Applying Discrete PCA in Data Analysis", in UAI '04: Proceedings of the 20th conference on Uncertainty in artificial intelligence, 2004, pp. 59-66.
Clark, "Inference ofhaplotypes from PCR-amplified samples of diploid populations", Mol. Biol. Evol. 7, 111-122 (1990).
Consortium, "A second generation human haplotype map of over 3.1 million snps", Nature 449, 851-61 (2007).

(Continued)

*Primary Examiner* — Mary K Zeman
(74) *Attorney, Agent, or Firm* — KPPB LLP

(57) ABSTRACT

The present disclosure presents a unified system to phase a personal genome for downstream clinical interpretation. In an embodiment, an initial phasing is generated using public datasets, such as haplotypes from the 1000 Genomes Project, and a phasing toolkit. A local perturbation algorithm is applied to improve long range phasing. If available, a Mendelian inheritance pipeline is applied to identify phasing of novel and rare variants. These datasets are merged, followed by correction by any experimental data. This allows for full clinical interpretation of the role of a group of variants in a gene, whether inherited or de novo variants.

14 Claims, 8 Drawing Sheets

(56) References Cited

OTHER PUBLICATIONS

Efron et al., "Least Angle Regression", The Annals of Statistics, 2004, vol. 32, No. 2, pp. 407-499.
Eronen et al., "HaploRec: efficient and accurate large-scale resconstruction fo haplotypes", BMC Bioinformatics, 2006, 7:542, 18 pgs.
Excoffier et al., "Maximum-likelihood estimation of molecular haplotype frequencies in a diploid population", Mol Biol Evol 12, 921-927 (1995).
Falush et al., "Inference of Population Structure Using Multilocus Genotype Data: Linked Loci and Correlated Allele Frequencies", Genetics, Aug. 2003, vol. 164, pp. 1567-1587.
Frey et al., "Clustering by Passing Messages Between Data Points", Science, Feb. 16, 2007, vol. 315, pp. 972-976.
Friedman et al., "Pathwise Coordinate Optimization", The Annals of Applied Statistics, 2007, vol. 1, No. 2, pp. 302-332.
Greenspan et al., "Model-based Inference of Haplotype Block Variation", in Proceedings of he seventh annual international conference of Research in computational molecular biology, 2003. pp. 131-137.
Hancock et al., "Genome-wide association study implicates chromosome 9q21.31 as a susceptibility locus for asthma in mexican children", PLoS Genet. 5, e1000623 (2009).
Hawley et al., "HAPLO: A Program Using the EM Algorithm to Estimate the Frequencies of Multi-site Haplotypes", J Hered 86, 409-411 (1995).
Higasa et al., "Evaluation of haplotype inference using definitive haplotype data obtained from complete hydatidiform moles, and its significance for the analyses of positively selected regions", PLoS Genet 5, e1000468 (2009).
Hofling, "A path algorithm for the Fused Lasso Signal Approximator", Journal of Computational and Graphical Statistics, Oct. 2009, 39 pgs.
Hoggart et al., "Control of confounding of Genetic Associations in Stratified Populations.", Am. J. Hum. Genetic, 2003, 72, pp. 1492-1504.
Hoggart et al., "Design and Analysis of Admixture Mapping Studies", Am. J. Hum. Genet., 2004, 74, pp. 965-978.
Kim et al., "L1 Trend Filtering", SIAM Reviews, 2009, 51(2), pp. 339-360.
Kimmel et al., "GERBIL: Genotype resolution and block identification using likelihood", PNAS, Jan. 4, 2005, vol. 102, No. 1, pp. 158-162.
Kong et al., "Detection of sharing by descent, long-range phasing and haplotype imputation", Nature Genetics 40, 1068-75 (2008).
Kschischang et al., "Factor Graphs and the Sum-Product Algorithm", IEEE Transactions on Information Theory, Feb. 2001, vol. 47, No. 2, 498-519.
Lai et al., "Stochastic segmentation models for array based comparative genomic hybridization data analysis", Biostatistics 9, 290-307, (2008).
Lauritzen et al., "Local Computations with Probabilities on Graphical Structures and Their Application to Expert Systems", J.R. Statist. Soc., B, 1988, 50(2). pp. 157-224.
Li et al., "Modeling Linkage Disequilibrium and Identifying Recombination Hotspots Using Single-Nucleotide Polymorphism Data", Genetics, Dec. 2003, vol. 165, pp. 2213-2233.
Li et al., "Worldwide Human Relationships Inferred from Genome-Wide Patterns of Variation", Science, Feb. 22, 2008, vol. 319, pp. 1100-1104.
Long et al., "An E-M algorithm and testing strategy for multiple-locus haplotypes", Am J Hum Genet 56, 799-810 (1995).
Marchini et al., "A comparison of phasing algorithms for trios and unrelated individuals", American Journal of Human Genetics 78, 437-450 (2006).
Marchini et al., "A new multipoint method for genome-wide association studies by imputation of genotypes", Nature Genetics 39, 906-13 (2007).
McKeigue, "Mapping Genes That Underlie Ethnic Differences in Disease Risk: Methods for Detecting Linkage in Admixed Populations, by Conditioning on Parental Admixture", Am. J. Hum. Genet., 1998, 63, pp. 241-251.
McKeigue, "Mapping Genes Underlying Ethnic Differences in Disease Risk by Linkage Disequilibrium in Recently Admixed Populations", Am. J. Hum. Genet., 1997, vol. 60, pp. 188-196.
Montana et al., "Statistical Tests for Admixture Mapping with Case-Control and Cases-Only Data", Am. J. Hum. Genet., 2004, vol. 75, pp. 771-789.
Myers et al., "A fine-scale map of recombination rates and hotspots across the human genome", Science 310, 321-324 (2005).
Niu et al., "Bayesian haplotype inference for multiple linked single nucleotide polymorphisms", American Journal of Human Genetics 70, 157-169 (2002).
Novembre et al., "Genes mirror geography within Europe", Nature, Nov. 2008, vol. 456, 7 pgs.
Patterson et al., "Methods for High-Density Admixture Mapping of Disease Genes", Am. J. Hum. Genet., 2004, vol. 74, pp. 979-1000.
Patterson et al., "Population Structure and Eigenanalysis", PLoS Genetics, Dec. 2006, vol. 2, Issue 2, 20 pgs.
Pollak et al., "Nonlinear Evolution Equations as Fast and Exact solvers of Estimation Problems", IEEE Transactions on Signal Processing, Feb. 2005, vol. 53, No. 2, pp. 484-498.
Price et al., "Sensitive Detection of Chromosomal Segments of Distinct Ancestry in Admixed Populations", PLoS Genetics, Jun. 2009, vol. 5, Issue 6, 18 pgs.
Pritchard et al, "Inference of Population Structure Using Multilocus Genotype Data", Genetics, Jun. 2000, vol. 155, pp. 945-959.
Rabiner, "A tutorial on hidden markov models and selected applications in speech recognition", In Proceedings of the IEEE, 257-286 (1989).
Ron et al., "On the Learnability and Usage fo Acyclic Probabilistic Finite Auomata", COLT '95: Proceedings of the eighth annual conference on Computational learning theory, 1995, pp. 31-40.
Rosenberg et al., "Informativeness of Genetic Markers for Inference of Ancestry", Am. J. Hum. Genet., 2003, vol. 73, pp. 1402-1422.
Rudin et al., "Nonlinear total variation based noise removal algorithms", Physica D, 1992. vol. 60, pp. 259-268.
Sabeti et al., "Detecting recent positive selection in the human genome from haplotype structure", Nature 419, 832-7 (2002).
Sankararaman et al., "Estimating Local Ancestry in Admixed Populations", The American Journal of Human Genetics, Feb. 2008, vol. 82, pp. 290-303.
Sankararaman et al., "On the inference of ancestries in admixed populations", Genome Research, Apr. 2008, vol. 18, pp. 668-675.
Sardy et al., "On the Statistical Analysis of Smoothing by Maximizing Dirty Markov Random Field Posterior Distributions", Journal of the American Statistical Association, Mar. 2004, vol. 465, pp. 191-204.
Scheet et al., "A fast and flexible statistical model for largescale population genotype data: Applications to inferring missing genotypes and haplotypic phase", American Journal of Human Genetics 78, 629-644 (2006).
Stephens et al., "A new statistical method for haplotype reconstruction from population data", American Journal of Human Genetics 68, 978-89 (2001).
Stephens et al., "Accounting for decay oflinkage disequilibrium in haplotype inference and missing-data imputation", American Journal of Human Genetics 76, 449-462 (2005).
Sundquist et al., "Effect of genetic divergence in identifying ancestral origin using HAPAA", Genome Research, 2008, vol. 18, pp. 676-682.
Tang et al., "Estimation of Individual Admixture: Analytical and Study Design Considerations", Genetic Epidemiology, 2005, vol. 28, pp. 289-301.
Tang et al., "Reconstructing Genetic Ancestry Blocks in Admixed Individuals", The American Journal of Human Genetics, Jul. 2006, vol. 79, pp. 1-12.
Tian et al., "A Genomewide Single-Nucleotide-Polymorphism Panel for Mexican American Admixture Mapping", The American Journal of Human Genetics, Jun. 2007, vol. 80, pp. 1014-1023.

(56) References Cited

OTHER PUBLICATIONS

Tibshirani, "Regression Shrinkage and Selection via the Lasso", J. R. Statistical Soc. B, 1996, vol. 58, No. 1, pp. 267-288.
Tibshirani et al., "Sparsity and smoothness via the fused lasso", J.R. Statist. Soc. B, 2005, vol. 57, No. 1, pp. 91-108.
Tibshirani et al., "Spatial smoothing and hot spot detection for CDG14 data using the fused lasso", Biostatistics, 2008, vol. 9, No. 1, pp. 18-29.
Turner, "Functions to Perform Isotonic Regression", R package version, Jun. 1, 2015, 8 pgs.
Zakharia et al., "Characterizing the admixed African ancestry of African Americans", Genome Biology, 2009, 11 pgs.
Zhang et al., "A Hidden Markov Modeling Approach for Admixture Mapping Based on Case-Control Data", Genetic Epidemiology, 2004, vol. 27, pp. 225-239.
Zhu et al., "A classical likelihood based approach for admixture mapping using EM algorithm", Hum. Genet. 2006, vol. 120, pp. 431-445.
Hastie et al., "The Elements of Statistical Learning: Data Mining, Inference, and Prediction", Springer-Verlag, 2001, 3 pages.
Hofling, Holger, "Topics in Statistical Learning", PhD Thesis, Stanford University, May 2009, 144 pgs.
Zhu et al., "Linkage Analysis of a Complex Disease through Use of Admixed Populations", The American Journal of Human Genetics, vol. 74 , No. 6), 2004, pp. 1136-1153.
Abecasis et al., "Merline—rapid analysis of dense genetic maps using sparse gene flow trees", Nature Genetics, Jan. 2002, vol. 30, pp. 97-101.
Adzhubei et al., "A method and server for predicting damaging missense mutations", Nature Methods, vol. 7, No. 4, Apr. 2010, pp. 248-249.
Ashley et al., "Clinical evaluation incorporating a personal genome", Lancet, vol. 375, No. 9725, May 1, 2010, pp. 1525-1535; doi:10.1016/S0140-6736(10)60452-7.
Baudat et al., "PRDM9 is a major determinant of meiotic recombination hotspots in humans and mice", Science, vol. 327, Feb. 12, 2010, pp. 836-840.
Bentley et al., "Accurate whole human genome sequencing using reversible terminator chemistry", Nature, Articles, Nov. 6, 2008, vol. 456, pp. 53-59.
Bezemer et al., "No association between the common MTHFR 677C→T polymorphism and venous thrombosis: results from the MEGA study", Arch Intern Med, vol. 167, Mar. 12, 2007, pp. 497-501.
Bodenreider, "The Unified Medical Language System (UMLS): integrating biomedical terminology", Nucleic Acids Research, 2004, vol. 32, pp. D267-D270.
Broman et al., "Comprehensive human genetic maps: individual and sex-specific variation in recombination", The American Journal of Human Genetics, vol. 63, Aug. 7, 1998, pp. 861-869.
Chamary et al., "Hearing silence: non-neutral evolution at synonymous sites in mammals", Nature Reviews Genetics, Feb. 2006, vol. 7, pp. 98-108.
Chen et al., "The reference human genome demonstrates high risk of type 1 diabetes and other disorders", Pacific Symposium on Biocomputing, 2011, pp. 231-242.
De Bakker et al., "A high-resolution HLA and SNP haplotype map for disease association studies in the extended human MHC", Nature Genetics, vol. 38, No. 10, Oct. 2006, pp. 1166-1172.
Donnelly, "The Probability that Related Individuals Share Some Section of Genome Identical by Descent", Theoretical Population Biology, 1983, vol. 23, pp. 34-63.
Durbin et al., "A map of human genome variation from population-scale sequencing", Nature, vol. 467, Oct. 28, 2010, pp. 1061-1073.
Eyre-Walker, "An analysis of codon usage in mammals: selection or mutation bias?", Journal of Molecular Evolution, May 13, 1991, vol. 33, pp. 442-449.
Fitch, "Toward Defining the Course of Evolution: Minimum Change for a Specific Tree Topology", Systematic Zoology, Dec. 1971, vol. 20, No. 4, pp. 406-416.

Hofacker, "Vienna RNA secondary structure server", Nucleic Acids Research, Apr. 5, 2003, vol. 31, No. 13, pp. 3429-3431.
Hoppe et al., "Marburg I polymorphism of factor VII-activating protease is associated with idiopathic venous thromboembolism", Blood, Feb. 15, 2005, vol. 105, No. 4, pp. 1549-1551.
Ikemura, "Codon usage and tRNA content in unicellular and multicellular organisms", Molecular Biology and Evolution, vol. 2, No. 1, 1985, pp. 13-34.
Johnson et al., "SNAP: a web-based tool for identification and annotation of proxy SNPs using HapMap", Bioinformatics, Oct. 30, 2008, vol. 24, No. 24, pp. 2938-2939.
Kimchi-Sarfaty et al., "A "Silent" Polymorphism in the MDR1 Gene Changes Substrate Specificity", Science, Jan. 26, 2007, vol. 315, No. 5811, pp. 525-528.
Kimura, "Evolutionary rate at the molecular level", Nature, vol. 217, Feb. 17, 1968, pp. 624-626.
Klein et al., "Estimation of the warfarin dose with clinical and pharmacogenetic data", New England Journal of Medicine, vol. 360, No. 8, Feb. 19, 2009, pp. 753-764.
Kong et al., "Fine-scale recombination rate differences between sexes, populations and individuals", Nature, vol. 467, Oct. 28, 2010, pp. 1099-1103.
Kong et al., "Parental origin of sequence variants associated with complex diseases", Nature, vol. 462, No. 7275, Dec. 17, 2009, pp. 868-874.
Kong et al., "Sequence variants in the RNF212 gene associate with genome-wide recombination rate", Science, vol. 319, Mar. 7, 2008, pp. 1398-1401.
Koster et al., "Venous thrombosis due to poor anticoagulant response to activated protein C: Leiden Thrombophilia Study", Lancet, Dec. 18/25, 1993, vol. 342, pp. 1503-1506.
Kruglyak et al., "Parametric and Nonparametric Linkage Analysis: A Unified Multipoint Approach", The American Journal of Human Genetics, 1996, vol. 58, pp. 1347-1363.
Kujovich, "Factor V Leiden thrombophilia", Genetics in Medicine, Jan. 2011, vol. 13, No. 1, pp. 1-16.
Kumar et al., "Positional conservation and amino acids shape the correct diagnosis and population frequencies of benign and damaging personal amino acid mutations", Genome Research, 2009, vol. 19, pp. 1562-1569.
Li et al., "Fast and accurate short read alignment with Burrows-Wheeler transform", Bioinformatics, May 18, 2009, vol. 25, No. 14, pp. 1754-1760.
Macaya et al., "A synonymous mutation in TCOF1 causes Treacher Collins syndrome due to mis-splicing of a constitutive exon", American Journal of Medical Genetics Part A, Feb. 24, 2009, vol. 149A, pp. 1624-1627.
Marchini et al., "A new multipoint method for genome-wide association studies by imputation of genotypes", Nature Genetics, Jun. 17, 2007, vol. 39, No. 7, pp. 906-913.
Margaglione et al., "The methylenetetrahydrofolate reductase TT677 genotype is associated with venous thrombosis independently of the coexistence of the FV Leiden and the prothrombin A20210 mutation", Thrombosis and Haemostasis, vol. 79, 1998, pp. 907-911.
Morgan et al., "Likelihood ratios for genome medicine", Genome Medicine, 2010, vol. 2, No. 30, 5 pgs.
Myers et al., "Drive against hotspot motifs in primates implicates the PRDM9 gene in meiotic recombination", Science, vol. 327, Feb. 12, 2010, pp. 876-879.
Nachman et al., "Estimate of the Mutation Rate per Nucleotide in Humans", Genetics, Sep. 2000, vol. 156, pp. 297-304.
Nelson et al., "The Population Reference Sample, POPRES: a resource for population, disease, and pharmacological genetics research", The American Journal of Human Genetics, vol. 83, Sep. 12, 2008, pp. 347-358.
Ng et al., "Accounting for Human Polymorphisms Predicted to Affect Protein Function", Genome Research, 2002, vol. 12, pp. 436-446.
Ng et al., "Predicting the Effects of Amino Acid Substitutions on Protein Function", Annual Review of Genomics and Human Genetics, 2006, vol. 7, pp. 61-80.

(56) References Cited

OTHER PUBLICATIONS

Ng et al., "SIFT: Predicting amino acid changes that affect protein function", Nucleic Acids Research, vol. 31, No. 13, Feb. 28, 2003, pp. 3812-3814.

Ormond et al., "Challenges in the clinical application of whole-genome sequencing", Lancet, vol. 375, May 15, 2010, published online Apr. 30, 2010, pp. 1749-1751.

Paigen et al., "The recombinational anatomy of a mouse chromosome", PLoS Genetics, Jul. 2008, vol. 4, Issue 7, Article e1000119, 15 pgs., doi: 10.1371/journal.pgen.1000119.

Parvanov et al., "Prdm9 controls activation of mammalian recombination hotspots", Science, Feb. 12, 2010, vol. 327, No. 5967, Article 835; 4 pgs., doi:10.1126/science.1181495.

Petkov et al., "Crossover interference underlies sex differences in recombination rates", Trends in Genetics, vol. 23, No. 11, Oct. 26, 2007, pp. 539-542.

Price et al., "Principal components analysis corrects for stratification in genome-wide associate studies", Nature Genetics, Aug. 2006, vol. 38, No. 8, pp. 904-909.

Pruitt et al., "NCBI reference sequences (RefSeq): a curated non-redundant sequence database of genomes, transcripts and proteins", Nucleic Acids Research, vol. 35, 2007, published online Nov. 27, 2006, pp. D61-D65, doi:10.1093/nar/gkl842.

Purcell et al., "PLINK: A Tool Set for Whole-Genome Association and Population-Based Linkage Analyses", The American Journal of Human Genetics, Sep. 2007, vol. 81, pp. 559-575.

Ridker et al., "Interrelation of hyperhomocyst(e)inemia, factor V Leiden, and risk of future venous thromboembolism", Circulation, 1997, vol. 95, 1777-1782.

Ridker et al., "Mutation in the gene coding for coagulation factor V and the risk of myocardial infarction, stroke, and venous thrombosis in apparently healthy men", The New England Journal of Medicine, vol. 332, No. 13, Apr. 6, 1995, pp. 912-917.

Rivas et al., "Secondary structure alone is generally not statistically significant for the detection of noncoding RNAs", Bioinformatics, vol. 16, No. 7, 2000, pp. 583-605.

Roach et al., "Analysis of genetic inheritance in a family quartet by whole-genome sequencing", Science, vol. 328, Apr. 30, 2010, pp. 636-639.

Roemisch et al., "The frequent *Marburg I* polymorphism impairs the pro-urokinase activating potency of the factor VII activating protease (FSAP)", Blood Coagulation and Fibrinolysis, vol. 13, Apr. 3, 2002, pp. 433-441.

Sedding et al., "The G534E polymorphism of the gene encoding the factor VII-activating protease is associated with cardiovascular risk due to increased neointima formation", The Journal of Experimental Medicine, vol. 203, No. 13, Dec. 25, 2006, pp. 2801-2807.

Smith et al., "Mutations in ATP6N1B, encoding a new kidney vacuolar proton pump 116-kD subunit, cause recessive distal renal tubular acidosis with preserved hearing", Nature Genetics, vol. 26, Sep. 2000, pp. 71-75.

Sunyaev et al., "PSIC: profile extraction from sequence alignments with position-specific counts of independent observations", Protein Engineering, 1999, vol. 12, No. 5, pp. 387-394.

Vasen et al., "New Clinical Criteria for Hereditary Nonpolyposis Colorectal Cancer (HNPCC, Lynch Syndrome) Proposed by the International Collaborative Group on HNPCC", Gastroenterology, 1999, vol. 116, pp. 1453-1456.

Watterson, "On the number of segregating sites in genetical models without recombination", Theoretical Population Biology, vol. 7, 1975, pp. 256-276.

Williams et al, "Rapid haplotype inference for nuclear families", Genome Biology, 2010, vol. 11, No. R108, 17 pgs.

Yeo et al., "Maximum entropy modeling of short sequence motifs with applications to RNA splicing signals", Journal of Computational Biology, Feb, 2004, vol. 11, No. 2-3. pp. 377-394.

Zhang et al., "Generic Algorithm to Predict the Speed of Translational Elongation: Implications for Protein Biogenesis", PLoS ONE, Apr. 3, 2009, vol. 4, Issue 4, No. e5036, pp. 1-9, doi: 1 0.137-journal.pone.0005036.

Ramensky et al., "Human non-synonymous SNPs: server and survey", Nucleic Acids Research, 2002, vol. 30, No. 17, pp. 3894-3900.

* cited by examiner

Table 1

| | FastPHASE | FastPHASE+PHASE-EM | Beagle | Beagle+PHASE-EM | column 2 / column 1 |
|---|---|---|---|---|---|
| CEU | 0.0606 | 0.0474 | 0.0673 | 0.0501 | 0.7826 |
| MEX | 0.0488 | 0.0419 | 0.0586 | 0.0440 | 0.8587 |
| YRI | 0.0927 | 0.0600 | 0.1020 | 0.0620 | 0.6471 |

Fig. 5

Table 2

| # chromsomes | FastPHASE | FastPHASE+PHASE-EM | Beagle | Beagle+PHASE-EM |
|---|---|---|---|---|
| 200 | 0.049 | 0.042 | 0.050 | 0.044 |
| 400 | 0.045 | 0.036 | 0.048 | 0.036 |
| 800 | 0.042 | 0.030 | 0.040 | 0.030 |
| 1200 | 0.042 | 0.027 | 0.036 | 0.026 |
| 1968 | 0.041 | 0.023 | 0.032 | 0.022 |

METHOD AND SYSTEM FOR PHASING INDIVIDUAL GENOMES IN THE CONTEXT OF CLINICAL INTERPRETATION

CROSS-REFERENCE TO RELATED APPLICATIONS

This application claims priority to U.S. Provisional Application No. 61/492,365 filed Jun. 1, 2011, which is hereby incorporated by reference in its entirety for all purposes.

STATEMENT OF GOVERNMENT SPONSORED SUPPORT

This invention was made with Government support under contracts GM073059 and HG002357 awarded by the National Institutes of Health. The Government has certain rights in this invention.

FIELD OF THE INVENTION

The present invention generally relates to the field of computer diagnostics. More particularly, the present invention relates to methods for analyzing a genome.

BACKGROUND OF THE INVENTION

The term haplotype refers to the combination of alleles at multiple loci along a chromosome. In linkage disequilibrium (LD) mapping, haplotype-based tests are thought to improve power for detecting untyped variants. In population genetics studies of evolutionary histories, haplotype data have been used to detect recombination hotspots as well as regions that have undergone recent positive selection (Myers, S., Bottolo, L., Freeman, C., McVean, G. & Donnelly, P. A fine-scale map of recombination rates and hotspots across the human genome. Science 310, 321-324 (2005); Sabeti, P. C. et al. Detecting recent positive selection in the human genome from haplotype structure. Nature 419, 832-7 (2002); these and all other references cited herein are incorporated by reference for all purposes). Despite its usefulness, haplotypes cannot be directly assayed using existing high-throughput genomic or sequencing technologies which instead generate genotype data-unordered pairs of alleles. While reconstructing haplotype from genotypes is straightforward in some special settings (e.g. in the presence of relatives, in sperm, or for X chromosomes in males), statistical inference of haplotype from autosomal genotype data with no known relatives is challenging.

The paper by Kong et al (Kong, A. et al. Detection of sharing by descent, long-range phasing and haplotype imputation. Nature Genetics 40, 1068-75 (2008)) showed that distantly related individuals can be used accurately to infer haplotype phase from genotypes. Individuals sharing long haplotypes, "pseudo parents," could be used to phase each other just as the two parents in a trio can be used to phase the unordered genotypes of their offspring. They showed an impressive performance improvement over an existing algorithm, FastPHASE (Scheet, P. & Stephens, M. A fast and flexible statistical model for largescale population genotype data: Applications to inferring missing genotypes and haplotypic phase. American Journal of Human Genetics 78, 629-644 (2006)), but due to high computational burden could not compare against the related PHASE 2.1.1 algorithm (Stephens, M., Smith, N. & Donnelly, P. A new statistical method for haplotype reconstruction from population data. American Journal of Human Genetics 68, 978-89 (2001)).

Numerous methods have been developed to infer haplotypes. The method of Clark, A. G. Inference of haplotypes from PCR-amplified samples of diploid populations. Mol. Biol. Evol. 7, 111-122 (1990) begins by identifying a pool of unambiguous (homozygous) individuals, and phases the remaining individuals based on a parsimony heuristic that seeks to minimize the total number of distinct haplotypes in the sample. For a small number of linked markers, multi-nomial-based model fit by the Expectation-Maximization (EM) algorithms can be quite effective (Excoffier, L. & Slatkin, M. Maximum-likelihood estimation of molecular haplotype frequencies in a diploid population. Mol Biol Evol 12, 921-927 (1995); Hawley, M. E. & Kidd, K. K. Haplo: a program using the em algorithm to estimate the frequencies of multi-site haplotypes. J Hered 86, 409-411 (1995); Long, J. C., Williams, R. C. & Urbanek, M. An E-M algorithm and testing strategy for multiple-locus haplotypes. Am J Hum Genet 56, 799-810 (1995)). The partition-ligation (PL-EM) algorithm of (Niu, T., Qin, Z. S., Xu, X. & Liu, J. S. Bayesian haplotype inference for multiple linked single nucleotide polymorphisms. American Journal of Human Genetics 70, 157-169 (2002)) was proposed to accelerate computation, and to keep the EM algorithm from becoming trapped in poor local modes. These methods identify common haplotypes. However, the multinomial model is inappropriate for rare haplotypes, which is a serious weakness because for any fixed sample size of individuals, a majority of haplotypes become rare or unique as the number of marker increases—either by increasing marker density or by expanding the genomic region.

SUMMARY OF THE INVENTION

An important feature of the phasing problem, which was ignored by the early methods, is that all haplotypes are related through a genealogy; as such a "rare" haplotype that resembles a common haplotype is more plausible than a "rare" haplotype that resembles no other observed haplotype. The coalescent-based likelihood function underlying the PHASE program has followed (Stephens, M., Smith, N. & Donnelly, P. A new statistical method for haplotype reconstruction from population data. American Journal of Human Genetics 68, 978-89 (2001)). Subsequently, PHASE 2.1.1 incorporates intermarker distance to account for the linkage disequilibrium (LD) between linked markers (Stephens, M. & Scheet, P. Accounting for decay of linkage disequilibrium in haplotype inference and missing-data imputation. American Journal of Human Genetics 76, 449-462 (2005)).

In the embodiments described below, discussions pertaining to PHASE refer to the latest version, PHASE 2.1.1, unless otherwise specified. In comparisons using simulated and real data, it was found that PHASE consistently outperforms other existing methods. When implemented via Markov Chain Monte Carlo algorithms (MCMC), PHASE is computationally intensive where it can be difficult to perform analysis of large-scale datasets, such as those generated in genome-wide association studies (GWAS). It should, nonetheless, be understood that other programs beyond PHASE can be implemented consistent with the teachings of the present invention as would be understood by those of ordinary skill in the art. An embodiment of the present invention is described herein as PHASE-EM. PHASE-EM will be used to describe features of the present invention, however, the present invention is not limited to the PHASE-EM embodiment.

In an embodiment of the present invention, a modified version of the PHASE model is implemented that is substantially more accurate than the FastPHASE model. Modifications in an embodiment of the present invention include using a parameterization EM algorithm similar to that of the FastPHASE model, and to perform optimization on haplotypes rather than MCMC sampling. In an embodiment, the imputed haplotypes themselves are used as hidden states in the HMM because this is believed to be important for the PHASE model's accuracy. This increase in accuracy becomes more pronounced with increasing sample size. This difference is attributed to the PHASE model's likelihood which produces long, shared haplotypes between pairs of individuals.

In another embodiment of the present invention, we argue that the concept of pseudo parents also underlies PHASE, and is a key difference between it and its successor Fast-PHASE. Using different computational techniques and a simplified parameterization, we show that PHASE can be applied to panels larger than previously possible, leading to substantial performance improvement over FastPHASE.

Personal genome sequencing is becoming more accessible to individuals in a clinical setting. Currently, the output of a genome sequencing service is done without context of familial inheritance and only provides a snapshot of mutations in a personal genome. Furthermore, several algorithms have been established to interpret a genome in a clinical context, but inheritance information can improve the interpretation of the specific role of each mutation or group of mutations. Phasing these genomes can be an integral part of determining the clinical relevance of rare and novel variants.

Currently, there is no cohesive method to incorporate multiple sources of data to phase a genome in the efforts of clinical interpretation of a personal genome. Phasing variants would allow us to assign greater confidence to the contribution of a group of variants on a potential clinical phenotype.

The present disclosure presents a unified system to phase a personal genome for downstream clinical interpretation. In an embodiment, an initial phasing is generated using public datasets, such as haplotypes from the 1000 Genomes Project, and a phasing toolkit. A local perturbation algorithm is applied to improve long range phasing. If available, a Mendelian inheritance pipeline is applied to identify phasing of novel and rare variants (not found in the public databases). These datasets are merged, followed by correction by any experimental data (including data from Complete Genomics on haplotyping and Paired-End Sequencing). This allows for full clinical interpretation of the role of a group of variants in a gene, whether inherited or de novo variants.

The output of a phased genome can then be applied in the context of clinical interpretation. For instance, if two variants are found in the same gene and on different alleles, the predicted phenotype may be more severe than two variants found on the same allele. Thus, phasing information can be incorporated to adjust the risk conferred by any single mutation or group of mutations.

The local perturbation algorithm improves long range phasing. Additionally, the present disclosure describes improvement to other methods by adding experimental paired-end sequencing data, which can capture the link between variants on paired reads (or on the same read). The application of an embodiment of the present invention to a personal genome can then add information about multiple variants found in the same gene.

We describe a local perturbation algorithm, as well as incorporating experimental data from paired end sequencing or Complete Genomics haplotype information. In the present disclosure, we describe how we apply this in a clinical context to ascertain the specific role of a mutation or group of mutations.

Currently, the methods of the present invention assume all calls are correct in the sequenced individuals. Alternatively, the present invention could incorporate quality information of a variant call to adjust the probability of inheritance from either parent. Additionally, inclusion of structural variation information (e.g. derived from paired-end reads) provides insight into the inheritance of larger-scale genome events in a clinical interpretation context in an embodiment of the invention.

These and other embodiments and advantages can be more fully appreciated upon an understanding of the detailed description of the invention as disclosed below in conjunction with the attached Figures.

BRIEF DESCRIPTION OF THE DRAWINGS

The following drawings will be used to more fully describe embodiments of the present invention.

FIG. 5 (Table 1) is a table of switch error rates corresponding to the three trio-panels used in FIG. 1 according to an embodiment of the present invention.

FIG. 6 (Table 2) is a table of error rates for the Mexican panel as a function of sample size according to an embodiment of the present invention.

DETAILED DESCRIPTION OF THE INVENTION

Figure 7:
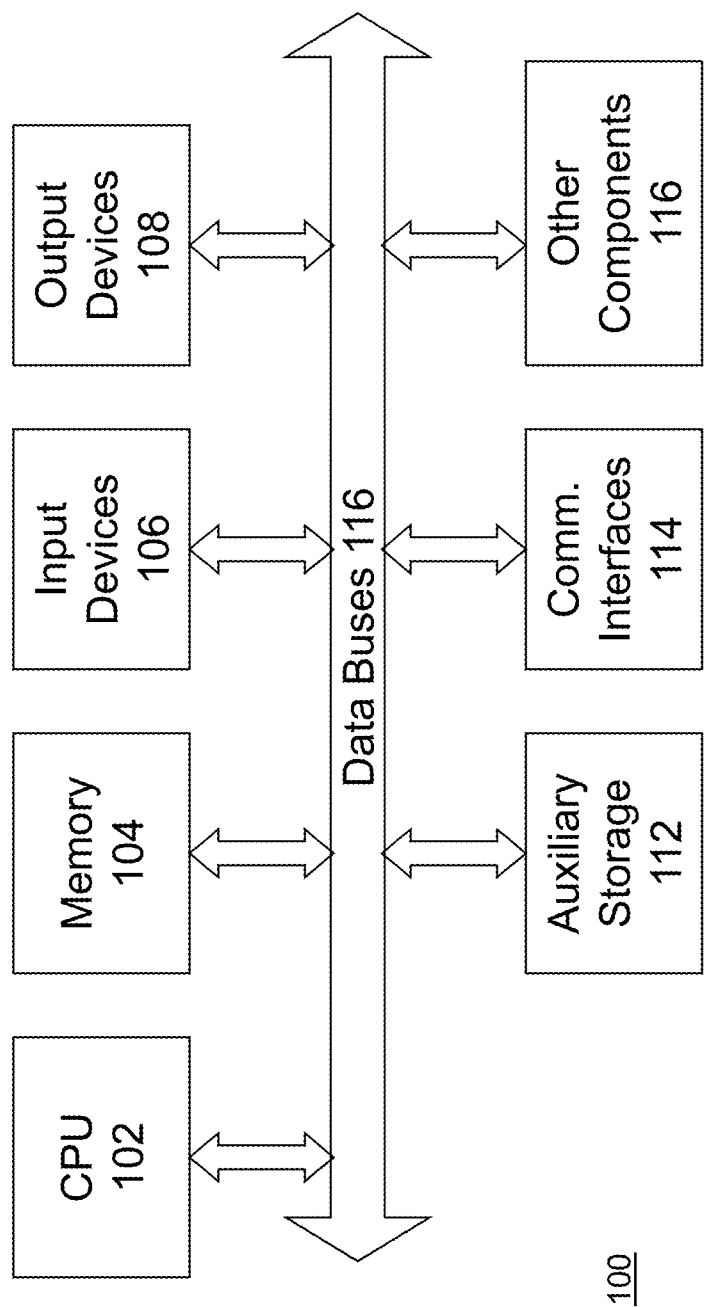
FIG. 7 is a block diagram of a computer system on which the present invention can be implemented.

Among other things, the present invention relates to methods, techniques, and algorithms that are intended to be implemented in a digital computer system 100 such as generally shown in FIG. 7. Such a digital computer is well-known in the art and may include the following.

Computer system 100 may include at least one central processing unit 102 but may include many processors or processing cores. Computer system 100 may further include memory 104 in different forms such as RAM, ROM, hard disk, optical drives, and removable drives that may further include drive controllers and other hardware. Auxiliary storage 112 may also be include that can be similar to memory 104 but may be more remotely incorporated such as in a distributed computer system with distributed memory capabilities.

Computer system 100 may further include at least one output device 108 such as a display unit, video hardware, or other peripherals (e.g., printer). At least one input device 106 may also be included in computer system 100 that may include a pointing device (e.g., mouse), a text input device (e.g., keyboard), or touch screen.

Communications interfaces 114 also form an important aspect of computer system 100 especially where computer system 100 is deployed as a distributed computer system. Computer interfaces 114 may include LAN network adapters, WAN network adapters, wireless interfaces, Bluetooth interfaces, modems and other networking interfaces as currently available and as may be developed in the future.

Computer system 100 may further include other components 116 that may be generally available components as well as specially developed components for implementation of the present invention. Importantly, computer system 100 incorporates various data buses 116 that are intended to allow for communication of the various components of computer system 100. Data buses 116 include, for example, input/output buses and bus controllers.

Indeed, the present invention is not limited to computer system 100 as known at the time of the invention. Instead, the present invention is intended to be deployed in future computer systems with more advanced technology that can make use of all aspects of the present invention. It is expected that computer technology will continue to advance but one of ordinary skill in the art will be able to take the present disclosure and implement the described teachings on the more advanced computers or other digital devices such as mobile telephones or "smart" televisions as they become available. Moreover, the present invention may be implemented on one or more distributed computers. Still further, the present invention may be implemented in various types of software languages including C, C++, and others. Also, one of ordinary skill in the art is familiar with compiling software source code into executable software that may be stored in various forms and in various media (e.g., magnetic, optical, solid state, etc.). One of ordinary skill in the art is familiar with the use of computers and software languages and, with an understanding of the present disclosure, will be able to implement the present teachings for use on a wide variety of computers.

The present disclosure provides a detailed explanation of the present invention with detailed explanations that allow one of ordinary skill in the art to implement the present invention into a computerized method. Certain of these and other details are not included in the present disclosure so as not to detract from the teachings presented herein but it is understood that one of ordinary skill in the art would be familiar with such details.

Using data in a cohort of 35,528 Icelandic individuals genotyped by deCode, (Kong, A. et al. Detection of sharing by descent, long-range phasing and haplotype imputation. Nature Genetics 40, 1068-75 (2008)) demonstrated that the accuracy of haplotypes inferred by FastPHASE is limited to a short range: the error rate rise to 30% for phasing a region of 6.4 Mb. This error rate is comparable to the individual error rate reported in Scheet et al. (Scheet, P. & Stephens, M. A fast and flexible statistical model for largescale population genotype data: Applications to inferring missing genotypes and haplotypic phase. American Journal of Human Genetics 78, 629-644 (2006)).

Kong et al. proposed long-range phasing method (LRP), which is based on the rationale that, in a large sample, some individuals may be closely related, such as second cousins. The LRP implements a heuristic algorithm that identifies "surrogate" parents, who share at least one allele identical-by-state (IBS) with the proband over an extremely long region (e.g. 1,000 consecutive SNPs). The phasing of the proband is inferred by constructing the two obligatory haplotypes that must be shared by his/her surrogate parents. The LRP method was successful for the deCode sample considered in Kong et al.: for the 10 Mb MHC region on chromosome 6, 87% of the individuals can be fully phased, and 7% of the remaining individuals can be phased for 90% of the heterozygous sites; overall, 93.7% of the heterozygous sites can be phased unambiguously. But in many human populations, randomly sampled individuals are on average much less closely related than they are in the Icelandic population. As a result, the LRP method will not apply because many individuals will find no "surrogate" parents in the sample, unless a substantial fraction of the population is sampled.

Higasi et al. genotyped 100 haploid Japanese genomes from complete hydatidiform moles (CHM), which arise when an empty egg with no nucleus is fertilized by a normal sperm (Higasa, K. et al. Evaluation of haplotype inference using definitive haplotype data obtained from complete hydatidiform moles, and its significance for the analyses of positively selected regions. PLoS Genet 5, e1000468 (2009)). By pairing these haplotypes into pseudo individuals and using FastPHASE and Beagle to recover phasing information, the study provided and estimate of the error rate for the HapMap Japanese population. When applying the Extended Haplotype Homozygosity (EHH) test to either haplotypes inferred by FastPHASE or the true CHM haplotypes, the authors found evidence of positive selection using the true, but not the inferred, haplotypes. This result highlights the need to improve accuracy in existing statistical methods for haplotype inference.

The PHASE model consist of a score $S(h_1, \ldots, h_N; \rho, \theta)$ on N imputed haplotypes $h_1, \ldots, h_N$ which are binary sequences of alleles and each is of the length L and $\rho$ and $\theta$ are parameters of a Hidden Markov Model (HMM) (Rabiner, L. R. A tutorial on hidden markov models and selected applications in speech recognition. In Proceedings of the IEEE, 257-286 (1989)). This score decomposes as $$\Sigma_{j=1}^{N} S(h_j; \{h_k\}_{k \neq j}, \rho, \theta)$$

where $$S(h_j; \{h_k\}_{k \neq j}, \rho, \theta)$$

is large if $h_j$ appears to be a mosaic of the other haplotypes $\{h_k\}_{k \neq j}$. The score when the imputed haplotypes share longer subsequences and will be particularly large if $h_j$ and $h_k$ (for some index k) are identical at every SNP. Given a large panel, the procedure of Kong et al. provides an excellent means of optimizing it in an embodiment of the present invention (Kong, A. et al. Detection of sharing by descent, long-range phasing and haplotype imputation. Nature Genetics 40, 1068-75 (2008)). Since panel sizes are generally much smaller, pseudo parents are not explicitly demarcated but recognize that this relationship is indeed present through the latent variables in the model.

Method

Model and Notations.

Figure 8:
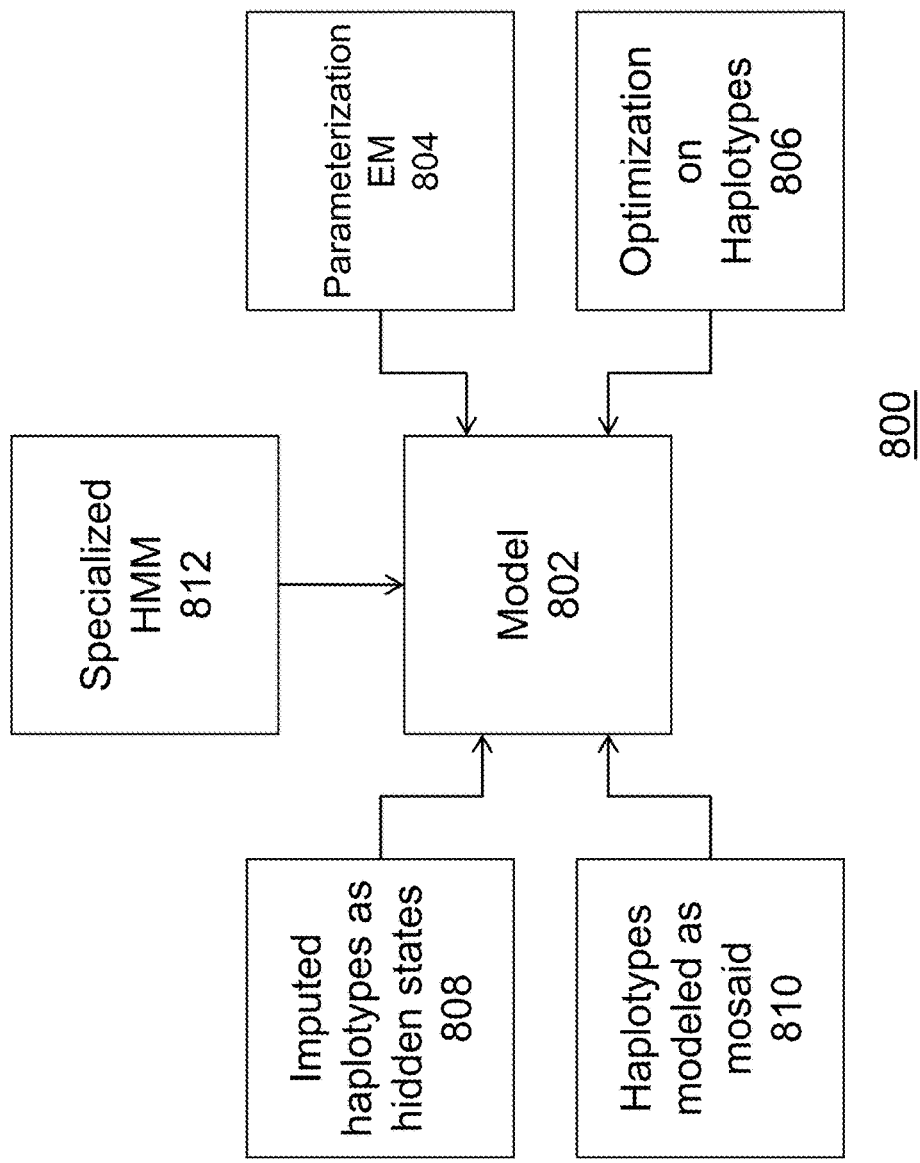
FIG. 8 is a block diagram describing feature of a specialized model to improve accuracy of haplotype detection in accordance with various embodiments of the invention.

Shown in FIG. 8 is a block diagram 800 describing features of a specialized model according to an embodiment of the present invention. As described below model 802 shown in FIG. 8 is substantially more accurate than the FastPHASE model. Modifications and improvements of an embodiment of the present invention are further shown in FIG. 8. For example, a model according to an embodiment of the present invention includes a parameterization EM algorithm 804. Also, an embodiment of the present invention perform an optimization on haplotypes 806 rather than MCMC sampling (such as in the "wphase" approach described in Marchini et al. (Marchini, J., Howie, B., Myers, S., McVean, G. & Donnelly, P. A new multipoint method for genome-wide association studies by imputation of genotypes. Nature Genetics 39, 906-13 (2007))). In the model according to an embodiment of the present invention, imputed haplotypes are used as hidden states (808) in the specialized HMM (812) to improve accuracy. This increase in accuracy becomes more pronounced with increasing sample size. This difference is attributed to the PHASE model's likelihood which produces long, shared haplotypes between pairs of individuals.

In an embodiment of the present invention, every haplotype in the sample is modeled as an imperfect mosaic of haplotypes from a haplotype pool (810). This idea can be illustrated using the following example. The HapMap phase III project genotyped 50 parent-offspring trios from the Yoruba population in Nigeria (YRI); the trio relationship allows the accurate phasing of the 200 parental haplotypes. This panel was used to phase a new sample, unrelated to any of the HapMap trios. An embodiment of the present invention seeks the most plausible configuration where the new haplotypes are derived from recombination and mutation events on the known HapMap haplotypes. To phase multiple individuals in the absence of an appropriately known haplotype pool, a method according to an embodiment of the present invention aims to jointly model all unobserved haplotypes based on the observed LD patterns. Specifically, an embodiment of the present invention achieves this by iteratively optimizing the phasing configuration for one individual, treating all the other individuals in the sample as phased.

In developing the model, let G denote the N by L matrix of genotypes for N diploid individuals genotyped at L SNP-markers; $G_{jk} \in \{0, 1, 2, ?\}$ corresponds to genotypes AA, AB, BB, and missing, respectively. The 2N by L matrix A is composed of imputed, phased haplotypes, and the rows $A_{2j-1}$ and $A_{2j}$ represent those from the jth individual. The matrix A is imputed data, but it also acts as model parameters. $A^{-j}$ is used to denote the matrix A with the jth individual's imputed haplotypes "removed" (for simplicity of notation, the row-indexing is left unchanged), and this submatrix acts as model parameters for the jth individual's haplotypes. A Hidden Markov Model (HMM) is developed having a hidden state sequence H, an emitted sequence B, and jump variables J. The emitted sequence $B_k$ is produced by taking the element of the current imputation $A_{Hk,k}$ and changing its value with a small probability θ. The conditional probabilities of the HMM (for the jth individual's haplotypes) are $$q_j(J_{k-1}=1;\rho_k)=\rho_k=1-q_j(J_{k-1}=0;\rho_k) \quad (1)$$

$$q_j(H_k=h|J_{k-1}=1,H_{k-1}=h')=1\{h\notin\{2j,2j-1\}\}/(2N-2) \quad (2)$$

$$q_j(H_k=h|J_{k-1}=0,H_{k-1}=h')=1\{h=h'\} \quad (3)$$

$$q_j(B_k=x|H_k=h;\theta_k,A^{-j})=1\{x\neq A_{h,k}\}(1-\theta_k)+1\{x=A_{h,k}\} \quad (4)$$

Figure 4:
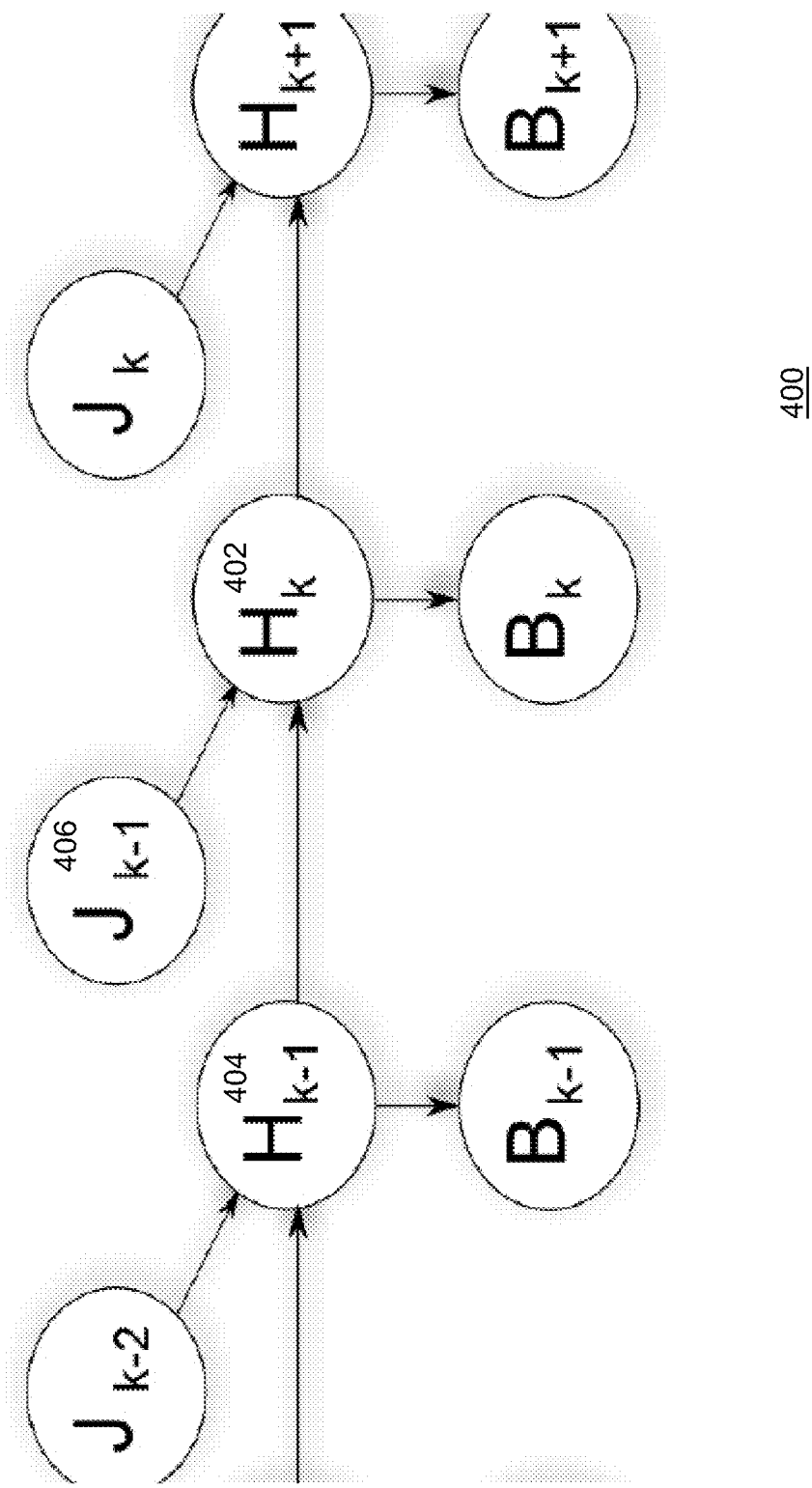
FIG. 4 is a representation of a Hidden Markov Model common to PHASE and FastPHASE according to an embodiment of the present invention.

Model parameters are placed after the semicolon to distinguish them from random variables. The first equation says that the jump variables $J_k$ are drawn as independent Bernoulli random variables. The next equations state that if the jump variable $J_k$ is zero, $H_{k+1}=H_k$ and the hidden state does not change. On the other hand if $J_k=1$, the next hidden state $H_k$ is drawn from a uniform distribution. As a result, the hidden state $H_k$ may "jump" but end up at $H_k$ anyway. FIG. 4 shows this HMM model 400 as a Bayesian network but does not explicitly show that $H_k$ 402 and $H_{k-1}$ 404 are independent conditional on $\{J_{k-1}$ (406)=1$\}$.

At each site, a hidden state emits one allele with high probability while emitting the other allele at the mutation rate, θ. The probability of a jump in hidden states between two consecutive markers is proportional to the local recombination rate, ρ. Using the physical distance between markers and a coalescent-based population genetics model, PHASE puts a prior on p, and jointly infers all aspects of the HMM by MCMC. In PHASE-EM as an embodiment of the present invention, the coalescent-based Bayesian prior is eliminated; as a consequence, the model parameters, ρ and θ, can be estimated by closed-form EM updates.

To make the equations above defined for k=1, $\rho_1=1$ and $H_0=1$, so that the dummy jump variable $J_0$ always equals 1. A complete and marginal likelihoods are now obtained where the dependence on the current phasing A is stressed:

$$q_j(B, J, H; \rho, \theta, A^{-j}) = \prod_{k=1}^{N} q_j(H_k | J_{k-1}, H_{k-1})q_j(B_k | H_k; \theta_k, A^{-j})q_j(J_{k-1}; \rho_k)$$

$$q_j(B; \rho, \theta, A^{-j}) = \sum_{J,H} \prod_{k=1}^{N} q_j(H_k | J_{k-1}, H_{k-1})q_j(B_k | H_k; \theta_k, A^{-j})q_j(J_{k-1}; \rho_k)$$

Following PHASE we will optimize the score $$S(A, \rho, \theta) := \sum_{j=1}^{N} \sum_{s=0}^{1} \log q_j(B = A_{2j-s,\cdot}; \rho, \theta, A^{-j}) \quad (5)$$

As implemented, the model above uses a simpler emission distribution, removes the divergence time variable T, and lacks Bayesian priors. In the model above as an embodiment of the present invention, the hidden states of the HMM are the imputed haploypes themselves. This is a primary difference between FastPHASE and the model above.

PHASE also has a random ordering v on the samples so that the parameters can be scored by a PAC-likelihood (PAC stands for Product of Approximate Conditionals). By simplifying the PHASE model, the primary reason that PHASE would be more accurate than FastPHASE can be identified. The PHASE model can capture longer range sharing without the need for complex hierarchical models.

To learn ρ and θ, the EM algorithm is used as in FastPHASE in an embodiment of the present invention. The score is no longer the likelihood of a single model, but by applying Jensen's inequality, it can be verified that the parameter updates defined below still increase the score S and optimize a minorizing Q-function as in the usual EM algorithm. The parameter updates are given as:

$$\rho_k \leftarrow \frac{\sum_{j=1}^{N} \sum_{s=0}^{1} q_j(J_{k-1} = 1 \mid B = A_{2j-s,\cdot}; A^{-j}, \theta, \rho)}{2N}$$

$$\theta_k \leftarrow \frac{\sum_{j=1}^{N} \sum_{s=0}^{1} \sum_{h=1}^{2N} 1\{A_{2j-s,k} \neq A_{h,k}\} q_j(H_k = h \mid B = A_{2j-s,\cdot}; A^{-j}, \theta, \rho)}{2N(2N-2)}$$

Recall from equation (2) that $$q_j(H_k=2j-s \mid B=A_{2j-s,\cdot}; A^{-j}, \theta, \rho)$$

for s=0, 1.

The Forward-Backward algorithm is used to compute the conditional probabilities above. On the order of ten parameter updates using a phasing A found by FastPHASE can be used. After the parameters are at reasonable values, parameter updates are interleaved with haplotype optimization described now. The parameters are held fixed, and a current phasing A is obtained. New haplotypes $C^1$, $C^2$ are then accepted for the jth individual based on the change in score $$\Delta(C^1, C^2, A_{2j-1,\cdot}, A_{2j,\cdot}) := \sum_{s=0}^{1} \log q_j(B = C^s; \rho, \theta, A^{-j}) \quad (6)$$

$$- \sum_{s=0}^{1} \log q_j(B = A_{2j-s,\cdot}; \rho, \theta, A^{-j}) \quad (7)$$

If $\Delta(C^1, C^2, A_{2k-1}, \ldots, A_{2j,\cdot})$ exceeds a nominal threshold (e.g., set to 0.3 in the present implementation that is an embodiment of the present invention), $A_{2j-1,\cdot} \leftarrow C^1$ and $A_{2k,\cdot} \leftarrow C^2$ are updated. Just as in PHASE, this update is made before optimizing haplotypes for any other individuals.

There are two basic optimizations on haplotypes that are performed. The first is a single site move in which $(A_{2j-1,t}, A_{2j,t})=(a, b)$ are set to be the highest scoring pair (a, b) that is compatible with the observed genotype $G_{jt}$. The second move is a crossover in which new haplotypes $C_k^1 = A_{2j-1\{k>t\},k}$ and $C_k^2 = A_{2j-1\{k<t\},k}$ are created. The proposed haplotype $C^1$ is the same as $A_{2j,\cdot}$ up to index t−1 and for larger indices it has the same sequence as $A_{2j-1,\cdot}$. Likewise the second haplotype $C^2$ in the proposed pair is identical $A_{2j-1,\cdot}$ at indices up to t−1 and to $A_{2j,\cdot}$ for larger indices. These moves are considered at every site t and are only made if they result in a non-negligible increase in the score S( ) over the current configuration.

Data Analysis.

Two trio datasets are used to assess the performance of an embodiment of the present invention to be described here. The parent-child family structure allows for inferring the two haplotypes in the children unambiguously at most markers, except triple heterozygous sites (e.g., both parents and the child are heterozygous) and sites where one or more individuals have missing genotypes. Knowing the haplotypes in the children, all haplotypes are inferred in the parents. These haplotypes, excluding ambiguous sites, are treated as the standard.

In an embodiment of the present invention, phasing methods are applied to the parents, without using the children's genotype. Results from these analyses are comparable to analyzing unrelated individuals. These parents' genotype data are analyzed using FastPHASE and Beagle separately. FastPHASE was run with 20 hidden states, 10 restarts, and 35 EM iterations per restart. Twenty hidden states, instead of the default setting of 10, were chosen because this gave a lower error rate. For Beagle, the default setting was used and the program was allowed to run for 10 iterations and took n=1 sample. Using the output of either FastPHASE or Beagle as starting points, the method is applied by fitting the model parameters for 10 iterations without changing the inferred haplotypes, followed by three more iterations of both updating the parameters and optimizing the haplotypes.

The first dataset consists of 45 CEU trios and 50 YRI trios, genotyped on the Illumina HumanHap650Y arrays as part of the International HapMap Project, Phase III (Consortium, T. I. H. A second generation human haplotype map of over 3.1 million snps. Nature 449, 851-61 (2007)). Specifically, focus is placed on the region of chromosome 9q, which included 13,976 SNPs. As a standard, the data that was used was the phased haplotype data generated by the HapMap consortium excluding ambiguous markers. In all analyses, the CEU and YRI trios were analyzed separately.

The second dataset includes 492 Mexican trios that were genotyped as part of an ongoing GWAS of asthma. The recruitment protocol was reviewed and approved by the Institute Review Boards of the Mexican National Institute of Public Health, the Hospital Infantil de Mexico, Federico Gomez, and the U.S. National Institute of Environmental Health Sciences. Parents provided the written informed consent for the child's participation. Children also gave their informed assent. The characteristics of this cohort are described previously (Hancock, D. B. et al. Genome-wide association study implicates chromosome 9q21.31 as a susceptibility locus for asthma in mexican children. PLoS Genet. 5, e1000623 (2009)). This dataset is useful for two reasons. First, it allows for assessing the performance of various phasing methods in an genetically admixed population, a subject that has not been systematically studied. Second, as described below, the accuracy of haplotype inference depends on the sample size; therefore, as one of the largest trio-sample that has been genotyped to date (984 parents), analyzing this data provides a more realistic measure of the phasing accuracy expected in a GWAS study.

Assessment of Accuracy.

It should be pointed out that most previous studies comparing haplotype inference methods have focused on the rate of switching error, which is the error probability between consecutive pairs of heterozygous sites. The switching error rate measures the short-range phasing accuracy and is useful in some applications such as estimation of local recombination rate. But other analyses, such as the extended haplotype homozygosity (EHH) test used for detecting recent positive selection, depend on accurate phasing over a longer range (see Sabeti, P. C. et al. Detecting recent positive selection in the human genome from haplotype structure. Nature 419, 832-7 (2002)). In these settings, the error rate between a random pair of SNPs, referred to as the individual error rate, is the relevant quantity. Furthermore, because a higher error rate is expected between markers that are far apart, it is useful to characterize the error rate as a function of distance.

In an embodiment, SNPs were indexed according to their physical positions, 1, 2, . . . , N, and define the distance between a pair of SNPs, i and j, by the difference in their indices, |i−j|. This metric was chosen because none of the methods otherwise considered here, FastPHASE, Beagle, and PHASE-EM, take into account physical or recombination distance. The error rate at distance, d, is then computed over all pairs of markers that are d SNPs apart.

Results

Two software packages are used to analyze large-scale high-density SNP data: FastPHASE (see Scheet, P. & Stephens, M. A fast and flexible statistical model for largescale population genotype data: Applications to inferring missing genotypes and haplotypic phase. American Journal of Human Genetics 78, 629-644 (2006)), and Beagle (see Browning, B. L. & Browning, S. R. A unified approach to genotype imputation and haplotype phase inference for large data sets of trios and unrelated individuals. American Journal of Human Genetics 84, 210-23 (2009)). Both programs employ Hidden Markov Models (HMM's), which can be computed efficiently via the EM algorithm and without lengthy MCMC runs.

FastPHASE implements a Markov Jump Model, in which the hidden states represent clusters of "similar" haplotypes. The number of hidden states is fixed and constant, and is usually set to a small number (e.g., 10-20) in practice. Similarly, Beagle represents local haplotype clusters by a directed acyclic graph (DAG). This graph is learned through a greedy algorithm and allows the number of hidden states to vary from region to region. Although the Beagle HMM typically has many more hidden states than that in FastPHASE, the computation in Beagle is not hampered because most hidden-state transition and emission probabilities are exactly zero.

Figure 1B:
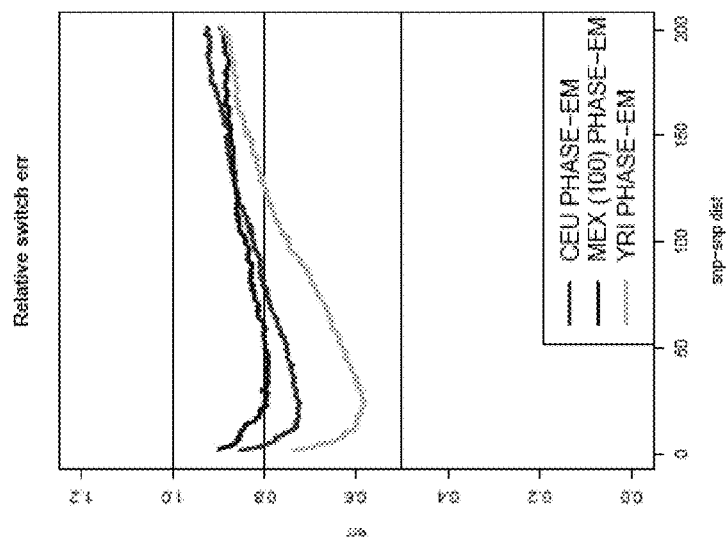
FIGS. 1A and 1B are graphs of phasing error rate as a function of marker index-distance according to an embodiment of the present invention.
Figure 1A:
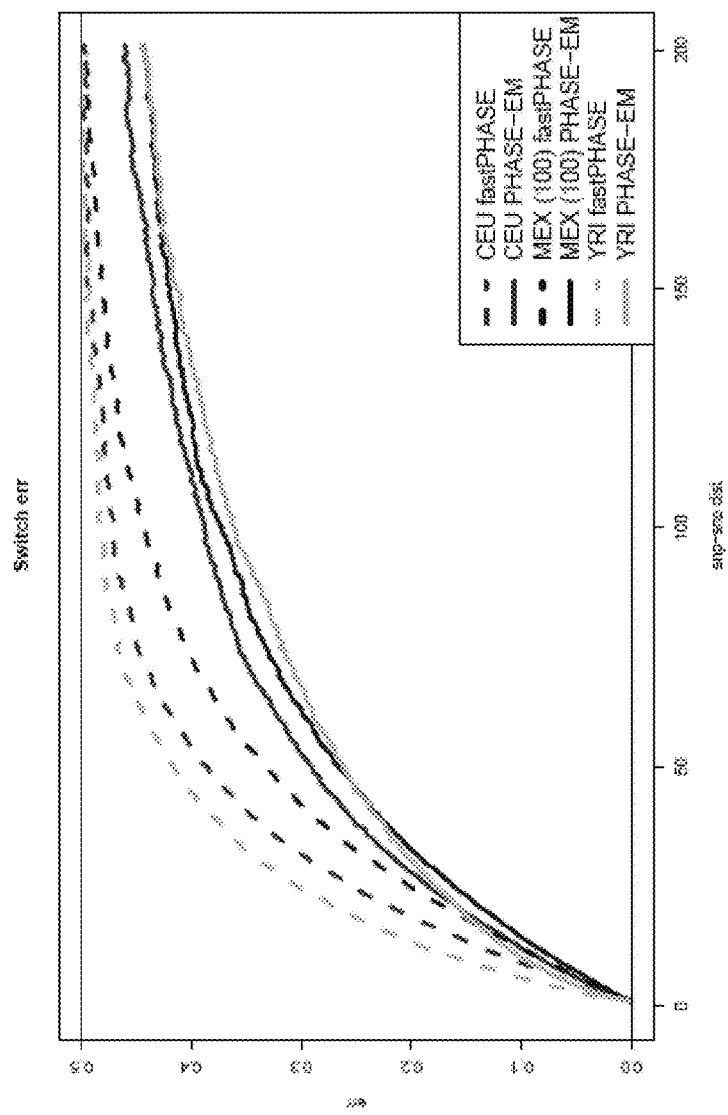
Figure 2B:
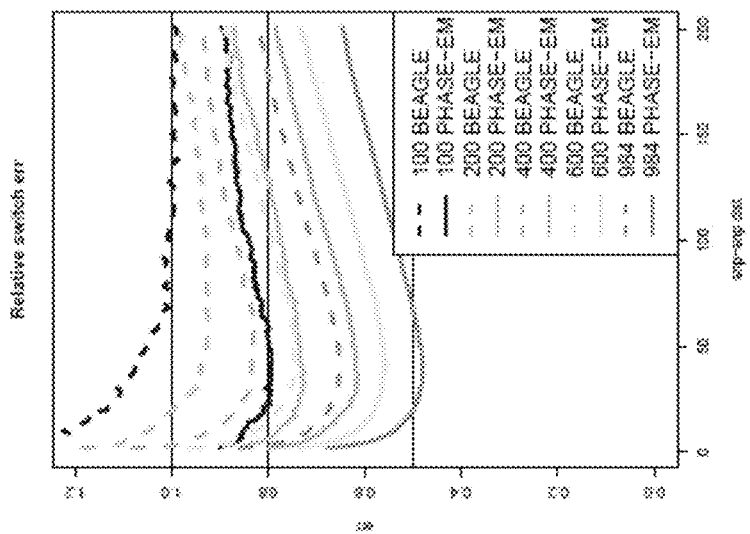
FIGS. 2A and 2B are graphs of phasing error as a function of sample size and inter-marker distance according to an embodiment of the present invention.
Figure 2A:
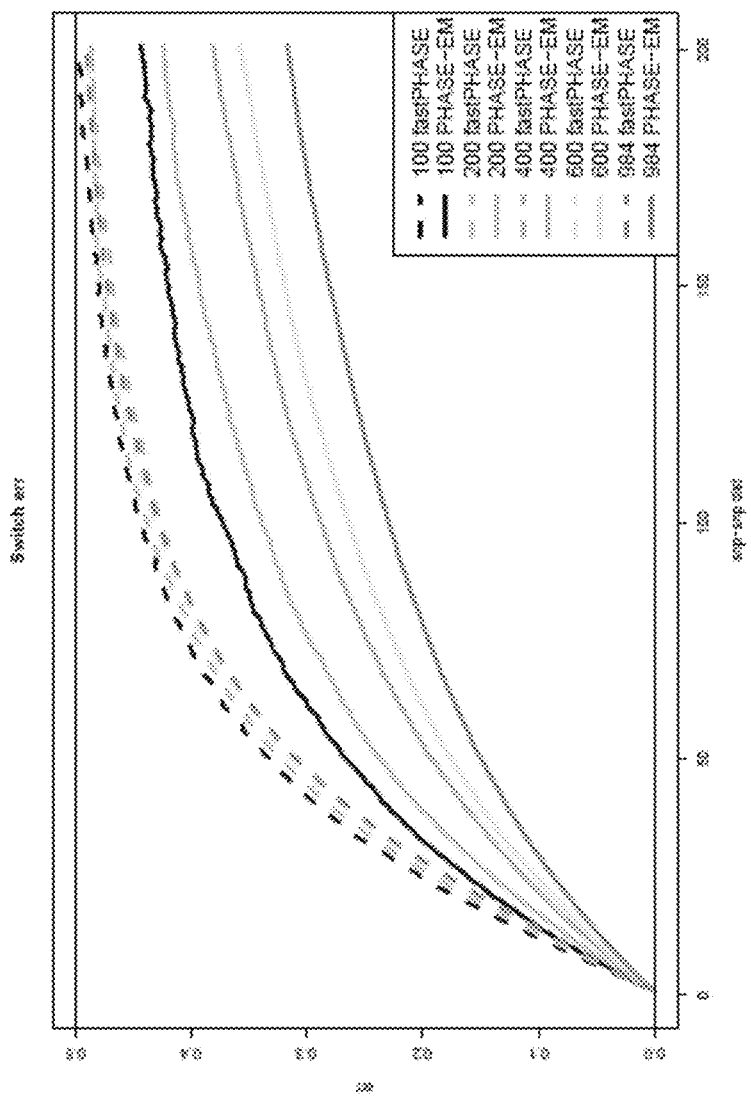

To assess the accuracy of PHASE-EM, haplotypes were inferred for the HapMap CEU and YRI parents as unrelated individuals, first using FastPHASE and subsequently updating the FastPHASE results with PHASE-EM. FIG. 1A compares the error rates generated by FastPHASE and PHASE-EM using trio-based phasing as the standard. As expected, the error rate increases with inter-marker distance, with the limit approaching the random guess error rate of 50%. On the CEU trio data, the error rate incurred by FastPHASE rises from 0.0165 to 0.0646 to 0.391 at snp's with index distance of 1, 5, and 50 respectively. Applying PHASE-EM to the output of FastPHASE, phasing accuracy improves regardless of marker distance; the reduction in error rate ranges between 10%-20% (see FIG. 1B), and is comparable with the difference between PHASE and FastPHASE found in (Lai, T. L., Xing, H. & Zhang, N. Stochastic segmentation models for arraybased comparative genomic hybridization data analysis. Biostatistics 9, 290-307 (2008)).

Analysis of the HapMap YRI dataset yields qualitatively similar results. But PHASE-EM achieves a greater error reduction on this set: between 20%-35% depending on the index distance. Even for adjacent SNP pairs, the PHASE-EM error rate is 26% lower than the FastPHASE error (0.031%). The greater improvement is due mainly to the higher error rate FastPHASE produces on the YRI data, which suggests that FastPHASE model with 20 states may be insufficient to model the level of haplotype diversity in an African population. In contrast, PHASE-EM achieves similar accuracy on the two datasets despite a poorer YRI starting configuration.

The difference between PHASE-EM and FastPHASE becomes more pronounced as the sample size is increased. In the subsample of 100 Mexican parents, a decrease in error rate is seen by about 10-20%. When PHASE-EM is run on larger data sets (400, 800, 1200 and 1968 chromosomes), this gap in performance widens considerably. Using the entire dataset, PHASE-EM nearly halved the error rate compared to FastPHASE. Increasing the sample size from 100 to 984, the switch error rate of FastPHASE dropped from 0.0477% to 0.0413% whereas PHASE-EM (initialized from these phasings) decreased from 0.0413% to 0.0236%. Beagle had an error rate of 0.0363% which also represents a significant gain in accuracy. However, despite the difference in switch error, almost no difference was found in the final PHASE-EM error-rate when initializing from Beagle rather than FastPHASE. This indicates that model refinements (such as the addition of the divergence time variable of PHASE) may be more important than better optimization moves. Table 2, shown in FIG. 6, shows the effect of sample size on the switch error rates.

In addition to inferring the most likely haplotype configurations, PHASE-EM produces two confidence measures as a bi-product of its optimization. Let $$\Delta_{jkk'}^{CR},$$

be a measure of uncertainty for the contiguous set of SNPs indexed k, k+1, . . . , k' in the jth imputed haplotype. This is the log likelihood of the imputed phasing minus the maximum log likelihood of a phasing after a single crossover is performed somewhere between SNPs k and k'. To illustrate, shown in FIG. 3A is the switch error rate stratified by this confidence measure in the left panel. The error rate of FastPHASE is shown for comparison. Shown are the pairs of SNP's with index distance given on the x axis and whose confidence measure falls in the intervals $(-1, \infty)$, $(-5, -1]$ and $(-\infty, -5]$, respectively. A very negative number means that all crossovers resulted in significantly lower likelihood and so a switch error is less likely, and this is reflected in the error rates.

Figure 3B:
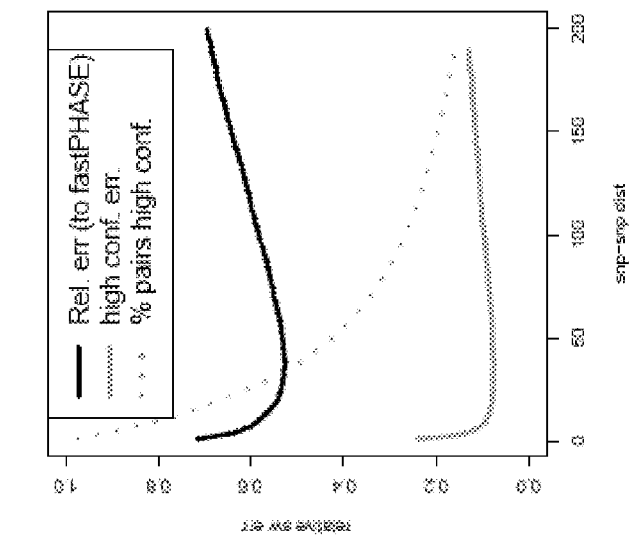
FIGS. 3A and 3B are graphs of error rate in the panel of 200 Mexican haplotypes using PHASE-EM according to an embodiment of the present invention.
Figure 3A:
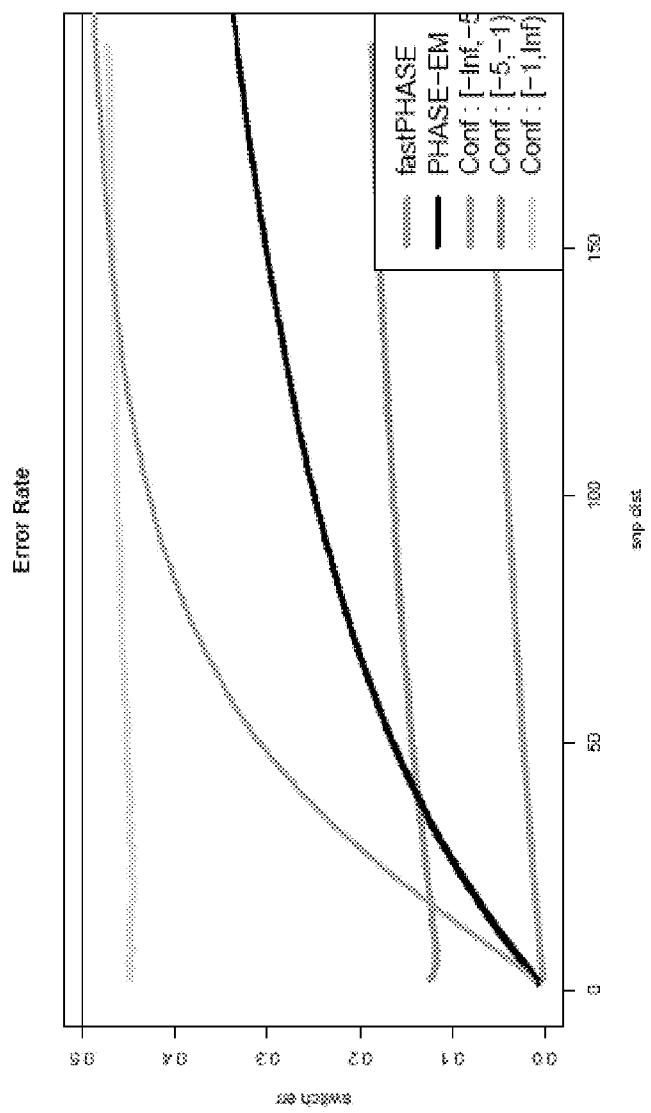

In FIG. 3, the dotted line indicates that fewer SNP-pairs fall in the high-confidence crossover stratum as the inter-marker distance increases; in the Mexican data, half of the SNP-pairs can be phased with high crossover confidence at a distance of 37 SNPs apart. The crossover measure allows for identifying a large set of long haplotypes that are still accurately phased. The usual switch error is also provided for these three panels in Table 1 shown in FIG. 5.

Discussion

The ability to accurately construct haplotypes from unphased genotype data plays pivotal roles in population and medical genetics studies. Previous studies have largely focused on accuracy over short range, such as the error rate between consecutive heterozygous sites (switching error), although some downstream analyses relies on accurate phasing over a long range (see Sabeti, P. C. et al. Detecting recent positive selection in the human genome from haplotype structure. Nature 419, 832-7 (2002)). In the present disclosure, a new method is disclosed, implemented in program PHASE-EM, with a goal to improve the long range phasing accuracy over FastPHASE and Beagle. The error rate is characterized as a function of marker spacing and observed that the error rate of FastPHASE, Beagle and PHASE-EM increase rapidly as a function of marker spacing. It is likely that a similar pattern holds for most other existing phasing algorithms with the exception of the heuristic-drive LRP method proposed in Kong et al. This latter method, however, relies on substantial pairs of individuals in the sample sharing haplotypes on the order of 1000. For this to hold, either the underlying population is extremely inbred or the sample size needs to be very large. The allele sharing is examined in 10 windows of 1000 SNPs in the HapMap CEU and YRI parents as well as the 984 Mexican parents and found no individual-pair sharing a haplotype at this length. Therefore, it is unlikely that LRP can be directly applied to data collected on non-founder populations.

Given that the error rate increases with an increase in distance between SNPs, it is can be important to account for the uncertainties in the downstream analysis. Two measures are disclosed: cross-over confidence and single-site confidence. The cross-over confidence was found to be highly informative while single-site confidence offers additional information. An analysis, such as the EHH, can be improved by accounting for the uncertainties.

The presently disclosed method relates to several other approaches. Like FastPHASE, Beagle, PHASE and many other methods, PHASE-EM, as an embodiment of the present invention, adopts an HMM model. A key feature in PHASE-EM is the hidden states of the HMM is every putative haplotype in the sample. There is a connection between this idea and the heuristic notion of "surrogate" parents that underlies LRP: the hidden state can be thought as the best "surrogate" parent; the optimization in PHASE-EM, which favors staying in a hidden state for long segments, coincides with features in LRP where long range allele sharing is a hallmark for "surrogate" parents. In other words, the HMM in PHASE-EM aims to choose the most-likely "surrogate" parents in the sample.

The success of the parameterization presented here indicates that the use of other haplotypes as hidden states for the HMM likelihood is an important difference between Fast-PHASE and PHASE. The PHASE model can simultaneously capture shared haplotypes at both local and large scales, and yet the model is not hierarchical. Some aspects of PHASE have been omitted which may improve performance (the divergence-time variable, for example), but it is useful to illustrate that the single retained aspect of PHASE produces more accurate phasings than FastPHASE.

In another embodiment of the present invention, we argue that the concept of pseudo parents also underlies PHASE, and is a key difference between it and its successor Fast-PHASE. Using different computational techniques and a simplified parameterization, we show that PHASE can be applied to panels larger than previously possible, leading to substantial performance improvement over FastPHASE.

Personal genome sequencing is becoming more accessible to individuals in a clinical setting. Currently, the output of a genome sequencing service is done without context of familial inheritance and only provides a snapshot of mutations in a personal genome. Furthermore, several algorithms have been established to interpret a genome in a clinical context, but inheritance information can improve the interpretation of the specific role of each mutation or group of mutations. Phasing these genomes can be an integral part of determining the clinical relevance of rare and novel variants.

Currently, there is no cohesive method to incorporate multiple sources of data to phase a genome in the efforts of clinical interpretation of a personal genome. Phasing variants would allow us to assign greater confidence to the contribution of a group of variants on a potential clinical phenotype.

The present disclosure presents a unified system to phase a personal genome for downstream clinical interpretation. In an embodiment, an initial phasing is generated using public datasets, such as haplotypes from the 1000 Genomes Project, and a phasing toolkit. A local perturbation algorithm is applied to improve long range phasing. If available, a Mendelian inheritance pipeline is applied to identify phasing of novel and rare variants (not found in the public databases). These datasets are merged, followed by correction by any experimental data (including data from Complete Genomics on haplotyping and Paired-End Sequencing). This allows for full clinical interpretation of the role of a group of variants in a gene, whether inherited or de novo variants.

The output of a phased genome can then be applied in the context of clinical interpretation. For instance, if two variants are found in the same gene and on different alleles, the predicted phenotype may be more severe than two variants found on the same allele. Thus, phasing information can be incorporated to adjust the risk conferred by any single mutation or group of mutations.

The local perturbation algorithm improves long range phasing. Additionally, the present disclosure describes improvement to other methods by adding experimental paired-end sequencing data, which can capture the link between variants on paired reads (or on the same read). The application of an embodiment of the present invention to a personal genome can then add information about multiple variants found in the same gene.

We describe a local perturbation algorithm, as well as incorporating experimental data from paired end sequencing or Complete Genomics haplotype information. In the present disclosure, we describe how we apply this in a clinical context to ascertain the specific role of a mutation or group of mutations.

Currently, the methods of the present invention assume all calls are correct in the sequenced individuals. Alternatively, the present invention could incorporate quality information of a variant call to adjust the probability of inheritance from either parent. Additionally, inclusion of structural variation information (e.g. derived from paired-end reads) provides insight into the inheritance of larger-scale genome events in a clinical interpretation context in an embodiment of the invention.

Further information regarding the present invention is included in Appendix 1 that is an excerpt from a thesis by Nicholas Johnson. See for example, Chapter 4.

Still further information regarding the present invention is included in Appendix 2 that is a presentation Hua Tang et al. that describes aspects of the present invention.

It should be appreciated by those skilled in the art that the specific embodiments disclosed above may be readily utilized as a basis for modifying or designing other algorithms or systems. It should also be appreciated by those skilled in the art that such modifications do not depart from the scope of the invention as set forth in the appended claims.

What is claimed is:

1. A computerized method for inferring a haplotype phase for an individual in a collection of unrelated individuals utilizing a dynamically linked matrix data structure, comprising:
    receiving unphased individual genotype data describing a human genotype for an individual from a database and storing the individual genotype data on a memory of a computer system;
    receiving genotype data describing human genotypes for a plurality of individuals from a database and storing the genotype data on a memory of a computer system;
    imputing an initial haplotype phase for the individual and each individual in the plurality of individuals based on a statistical model and storing the initial haplotype phase for each individual in the plurality of individuals on a computer system comprising a processor a memory;
    building a data structure describing a Hidden Markov Model, where the data structure contains:
        a set of predicted haplotype phases for each individual in the plurality of individuals; and a set of parameters comprising local recombination rates and mutation rates;

wherein any change to the set of predicted haplotype phases contained within the data structure automatically results in re-computation of the set of parameters comprising local recombination rates and mutation rates contained within the data structure;

repeatedly randomly modifying at least one of the predicted haplotype phases in the set of predicted haplotype phases to automatically re-compute a new set of parameters comprising local recombination rates and mutation rates that are stored within the data structure;

automatically replacing a predicted haplotype phase for an individual with a randomly modified haplotype phase within the data structure, when the new set of parameters indicate that the randomly modified haplotype phase is more likely than an existing predicted haplotype phase; and extracting at least one final predicted haplotype phases from the data structure as a phased haplotype for an individual; and storing the phased haplotype phase for the individual on a memory of a computer system.

2. The method of claim 1, wherein the initial haplotype phase for the individual and each individual in the plurality of individuals is imputed from a public dataset, and wherein the method further comprises applying a Mendelian inheritance pipeline to the haplotype phase for the individual using a computer system to generate a dataset identifying phasing variants of interest and storing the dataset in the memory of a computer system, where the Mendelian inheritance pipeline is a dataset comprising genetic variants associated with Mendelian disease.

3. The method of claim 1, further comprising correcting the haplotype phase for the individual using experimental data.

4. The method of claim 3, where experimental data is paired end sequencing data.

5. The method of claim 1, where the variants of interest are compound heterozygous.

6. The method of claim 1, further comprising optimizing the haplotype phase for the first individual by maximizing a score, where the score is based on identity between the haplotype phase for the individual and an imputed haplotype in the set of imputed haplotypes for the plurality of individuals.

7. The method of claim 6, where the score is S( ) where $$S(A, \rho, \theta) := \sum_{j=1}^{N} \sum_{s=0}^{1} \log q_j(B = A_{2j-s,\cdot}; \rho, \theta, A^{-j}),$$

where j is a sample index,
where B is an emitted haplotype sequence for the plurality of individuals, where the generated matrix is a matrix A, having dimensions 2N by L, where N is a number of genotypes for the plurality of individuals and L is a number of genetic markers, comprises the initial haplotype phase for each individual in the plurality of individuals stored in rows $A_{2j-1}$ and $A_{2j}$, where a matrix $A^{-j}$ is the matrix A with the initial haplotype phase for the particular individual removed, where $\rho$ is the local recombination rate, and
where $\theta$ is the mutation rate.

8. The method of claim 1, further comprising optimizing the haplotype phase for the first individual by selecting a single site move that results in a highest scoring pair for a genotype of the first individual, where the highest scoring pair results in a non-negligible increase in the score over a current configuration score.

9. The method of claim 8, where the non-negligible increase is 0.3.

10. The method of claim 8, further comprising determining a confidence measure for an optimized haplotype phase for the individual with respect to the single site switch by computing $\Delta_{jk}^{SS}$ at k and j, where the genotype of the first individual is missing, $\Delta_{jk}^{SS}$ is a maximum of a set of three alternative phased genotypes consisting of AA, AB, and BB where the genotype of the first individual is heterozygous, $\Delta_{jk}^{SS}$ is the log-likelihood ratio of a single, alternative phasing, where $\Delta_{jk}^{SS}$ is $$\Delta_{jk}^{SS} = \Sigma_{s=0}^{1} \log q_j(B=C^s;\rho,\theta,A^{-j}) - \Sigma_{s=0}^{1} \log q_j(B=A_{2j-s,\cdot};\rho,\theta A^{-j}),$$

where $C^s$ is a determined haplotype phase for the individual, and
where the genotype of the first individual is homozygous, the single site switch is ignored.

11. The method of claim 1, further comprising:
optimizing the haplotype phase for the individual by simulating a crossover by creating a crossover haplotype set consisting of a $C^1$ haplotype and a $C^2$ haplotype, where:
$C^1$ and $C^2$ are new haplotypes,
$C^1$ is identical to $A_{2j-1}$ up to index t−1, where t is a crossover site,
$C^2$ is identical to $A_{2j}$ up to index t−1, and
where crossover is considered at every site t and results in a non-negligible increase in a score of the crossover haplotype set over a current configuration score; and
updating $A_{2j-1}$ to $C^1$ and $A_{2j}$ to $C^2$.

12. The method of claim 11, where the non-negligible increase is 0.3.

13. The method of claim 11, further comprising determining a confidence measure for an optimized haplotype phase for the individual with respect to a crossover at k.

14. The method of claim 1 further comprising adjusting the risk conferred by at least one mutation for the individual based on the phased haplotype phase.

* * * * *